(12) United States Patent
Kenaan et al.

(10) Patent No.: US 10,744,091 B2
(45) Date of Patent: Aug. 18, 2020

(54) AMPHIPHILIC MOLECULES LAYERS (71) Applicants: CENTRE NATIONAL DE LA RECHERCHE SCIENTIFIQUE—CNRS, Paris (FR); Université d'Aix-Marseille, Marseilles (FR)

(72) Inventors: Ahmad Kenaan, Marseilles (FR); Anne Magali Charrier, Marseilles (FR); Sébastien Lavandier, Marseilles (FR); Jean-Manuel Raimundo, Carmoux en Provence (FR)

(73) Assignees: CENTRE NATIONAL DE LA RECHERCHE SCIENTIFIQUE—CNRS, Paris (FR); Université d'Aix-Marseille, Marseilles (FR)

( * ) Notice: Subject to any disclaimer, the term of this patent is extended or adjusted under 35 U.S.C. 154(b) by 0 days.

(21) Appl. No.: 15/768,471

(22) PCT Filed: Oct. 13, 2016

(86) PCT No.: PCT/EP2016/074569
§ 371 (c)(1),
(2) Date: Apr. 13, 2018

(87) PCT Pub. No.: WO2017/064176
PCT Pub. Date: Apr. 20, 2017

(65) Prior Publication Data
US 2019/0183799 A1    Jun. 20, 2019

(30) Foreign Application Priority Data
Oct. 16, 2015 (EP) ..................... 15306656

(51) Int. Cl.
A61K 9/127 (2006.01)
H01L 29/00 (2006.01)
(Continued)

(52) U.S. Cl.
CPC ............ *A61K 9/1273* (2013.01); *C08L 83/04* (2013.01); *A61K 9/1075* (2013.01); *C08G 77/42* (2013.01);
(Continued)

(58) Field of Classification Search
None
See application file for complete search history.

(56) References Cited

U.S. PATENT DOCUMENTS

2011/0190623 A1* 8/2011 Li ......................... A61K 9/127
                                                              600/420
2012/0052042 A1    3/2012 Ladet et al.
2014/0264473 A1    9/2014 Charrier et al.

OTHER PUBLICATIONS

Smith et al., Langmuir, 2014, vol. 30, pp. 3967-3704. (Year: 2014).*
(Continued)

*Primary Examiner* — Brian Gulledge
(74) *Attorney, Agent, or Firm* — Osha Liang LLP (57) ABSTRACT

The disclosure relates to a layer comprising at least one hydrophilic part and at least one hydrophobic part, the layer comprising self-assembled amphiphilic molecules polymerized with each other on both the hydrophilic part and the hydrophobic part of the layer; a detecting device comprising a substrate and the above-mentioned layer; and a liposome, a micelle, transport system for a substance and a biomimetic system comprising the above-mentioned layer. The disclosure also relates to a process for producing a layer, the process comprising: providing amphiphilic molecules; allowing sufficient time for the amphiphilic molecules to self-assemble and form at least one hydrophilic part and at least one hydrophobic part of the layer; polymerizing the
(Continued)

self-assembled amphiphilic molecules with each other on both the hydrophilic part and the hydrophobic part of the layer.

13 Claims, 3 Drawing Sheets

(51) Int. Cl.
    *C08L 83/04*       (2006.01)
    *A61K 9/107*     (2006.01)
    *C08G 77/42*     (2006.01)

(52) U.S. Cl.
    CPC ....... *C08L 2203/02* (2013.01); *C08L 2205/20* (2013.01)

(56) References Cited

OTHER PUBLICATIONS

International Search Report issued in PCT/EP2016/074569 dated Jan. 10, 2017 (3 pages).
Written Opinion of the International Searching Authority issued in PCT/EP2016/074569 dated Jan. 10, 2017 (7 pages).
El Zein, R. et al.; "Supported Lipid Monolayer with Improved Nonomechanical Stability: Effect of Polymerization"; The Journal of Physical Chemistry B, vol. 116, No. 24, Jun. 21, 2012, pp. 7190-7195 (6 pages).

\* cited by examiner

AMPHIPHILIC MOLECULES LAYERS

TECHNICAL FIELD

The present disclosure relates to amphiphilic molecules layers, detecting devices (e.g. sensors and biosensors), liposomes, micelles, transport systems and biomimetic systems comprising said layers, as well as processes for producing said layers.

BACKGROUND

Amphiphilic molecules are molecules possessing at least one hydrophilic moiety and at least one hydrophobic moiety, which may be used to form monolayers, bi-layers or multi-layers, such as in the form of micelles, liposomes, lamellar structures and the like, through self-assembly in a solvent and/or on a substrate.

Although amphiphilic molecules layers have some degree of chemical stability in aqueous media, the inherent chemical instability of amphiphilic molecules layers, such as lipid layers, when exposed to air, polar organic solvents and/or specific surfactants, limits their use in these media in advanced industrial processes. Accordingly, numerous studies have been performed in an attempt to provide chemically stable amphiphilic molecules layers in different media, for example by insertion of proteins, polymerization or fixation on substrates via covalent interactions.

During a previous work aimed at stabilizing monolayers by polymerization, the Applicant has found that supported amphiphilic molecules bearing apolar tails with two acetylenic groups may be two-dimensionally polymerized along a plane of the amphiphilic molecules to provide monolayers which are chemically stable also when exposed to air and a number of selected solvents. The Applicant has also found that a supported and polymerized monolayer may possess some degree of mechanical stability (see Anne M. Charrier et al., "*Supported Lipid Monolayer with Improved Nanomechanical Stability: Effect of Polymerization,*" J. Phys. Chem. B 2012, 116, 7190-7195).

Accordingly, there exists a continuing need to provide chemically and mechanically stable amphiphilic molecules layers, as well as detecting devices, liposomes, micelles, transport systems and biomimetic systems comprising said layers, and processes for producing said layers.

SUMMARY

An object of the present disclosure is to provide an amphiphilic molecules layer having improved chemical and mechanical stability. Another object of the present disclosure is to provide an amphiphilic molecules layer having improved electrical stability. A further object of the present disclosure is to provide a detecting device (e.g. sensor and biosensor), a liposome, a micelle, a transport system for a substrate and a biomimetic system, which comprise an amphiphilic molecules layer having improved mechanical and/or electrical stability.

According to a first aspect, the above-mentioned objects, as well as further advantages, are achieved by a layer comprising at least one hydrophilic part and at least one hydrophobic part, the layer comprising self-assembled amphiphilic molecules polymerized with each other on both the hydrophilic part and the hydrophobic part of the layer.

According to a second aspect, one or more of the above-mentioned objects, as well as further advantages, are achieved by a detecting device comprising a substrate and the layer according to the first aspect.

According to a third aspect, one or more of the above-mentioned objects, as well as further advantages, are achieved by a liposome, a micelle, a transport system for a substance and a biomimetic system comprising the layer according to the first aspect.

According to a fourth aspect, one or more of the above-mentioned objects, as well as further advantages, are achieved by a process for producing a layer, the process comprising: providing amphiphilic molecules; allowing sufficient time for the amphiphilic molecules to self-assemble and form at least one hydrophilic part and at least one hydrophobic part of the layer; and polymerizing the self-assembled amphiphilic molecules with each other on both the hydrophilic part and the hydrophobic part of the layer.

Embodiments of the present disclosure according to the above aspects are defined in the appended claims.

Other aspects and advantages of the present disclosure will be apparent from the following figures, description and appended claims.

BRIEF DESCRIPTION OF DRAWINGS

The present disclosure will be better understood and other advantages and embodiments will become clear on reading the description that follows, given purely by way of indication and in no way limiting, and by referring to the appended figures in which.

DETAILED DESCRIPTION OF EMBODIMENTS

Embodiments of the present disclosure will now be described in detail with reference to the accompanying figures. In the following detailed description of embodiments of the present disclosure, numerous specific details are set forth in order to provide a more thorough understanding of the present disclosure. However, it will be apparent to one of ordinary skill in the art that the present disclosure may be practiced without these specific details. In other instances, well-known features have not been described in detail to avoid unnecessarily complicating the description.

Herein, the terms "comprise/comprising" are synonymous with (means the same thing as) "include/including," "contain/containing", are inclusive or open-ended and do not exclude additional, non-recited elements. Further, herein the term "about" is synonymous with (means the same thing as) a 20 percent lower and/or higher margin of the respective value.

Herein, the term "polymerizing" is synonymous with (means the same thing as) providing an amphiphilic molecule polymer by connecting an amphiphilic $3o$ molecule monomer to another by covalent bonding (i.e., simple covalent bonding such as where each atom supplying at least one electron to the bond), optionally with a comonomer. Herein, the term "cross-linking," is synonymous with (means the same thing as) providing a cross-linked amphiphilic molecule polymer by polymerizing an amphiphilic molecule polymer to another by covalent bonding (i.e., simple covalent bonds), optionally with a cross-linking agent.

Herein, the term "biomolecule" is synonymous with (means the same thing as) a molecule that is present in or derived from living organisms.

According to one or more embodiments, the biomolecule is a molecule selected from the group comprising proteins, antibodies, polysaccharides, lipids, nucleic acids, metabolites, natural products and their analogues, parts thereof and sequences thereof. According to one or more embodiments, the biomolecule is selected from the group comprising proteins, DNAs, antibody, parts thereof and sequences thereof. Herein, the terms "natural product" are synonymous with (means the same thing as) a chemical compound or substance produced by a living organism. According to one or more embodiments, the protein is selected from the group comprising biotin and streptavidin. According to one or more embodiments, the DNA is selected from the group comprising single stranded DNA and aptamers.

The present disclosure relates to amphiphilic molecules, such as surfactants, for the fabrication of layers in the form of monolayers, bi-layers or multi-layers, with high chemical, mechanical and electrical stability. Specifically, according to the first aspect, the Applicant has found that a layer comprising at least one hydrophilic part and at least one hydrophobic part, wherein self-assembled amphiphilic molecules are polymerized with each other on both the hydrophilic part and the hydrophobic part of the layer, have improved chemical, mechanical and electrical stability. One of the technical effects achieved by embodiments according to the first aspect is to allow improved stiffness of the self-assembled amphiphilic molecules by reducing the spacing between the amphiphile molecules and reducing intramolecular movements of the hydrophilic part within the network of the self-assembled structure. In particular, a more confined network is obtained, which may prevent potential ions to penetrate within the network of the structure, thereby 3o improving the insulating properties of the layer. Further, polymerizing (e.g. by crosslinking) the amphiphilic molecules on the hydrophobic part allows maintaining the integrity of the structure. Polymerizing the hydrophilic part and the hydrophobic part also allows limiting the risks of breakdown of the electrical properties of the layer.

According to one or more embodiments, the self-assembled amphiphilic molecules form the at least one hydrophilic part and the at least one hydrophobic part of the layer, and the amphiphilic molecules are cross-linked on at least one of the hydrophilic part and the hydrophobic part. According to one or more embodiments, the amphiphilic molecules are polymerized on either one of the hydrophilic part and the hydrophobic part, and cross-linked on the other one of the hydrophilic part and the hydrophobic part.

According to one or more embodiments, the amphiphilic molecule comprises at least one hydrophilic head and at least one hydrophobic tail. According to one or more embodiments, the amphiphilic molecule comprises one hydrophilic head and two hydrophobic tails. According to one or more embodiments, the hydrophobic tails of the amphiphilic molecules are polymerized with each other, and the hydrophilic heads the hydrophobic tails of the amphiphilic molecules are polymerized with each other. According to one or more embodiments, the self-assembled amphiphilic molecules comprise polymerized hydrophobic tails and cross-linked hydrophilic heads.

According to one or more embodiments, the amphiphilic molecule comprises at least one heteroatom bound to a comonomer moiety or a cross-linker. According to one or more embodiments, the heteroatom is selected from the group comprising O, S, N and P. According to one or more embodiments, the heteroatom is oxygen. According to one or more embodiments, the heteroatom is on the hydrophilic head of the amphiphilic molecule.

According to one or more embodiments, the amphiphilic molecule comprises a surfactant. According to one or more embodiments, the surfactant is selected from the group comprising lipids, soaps, detergents, wetting agents, dispersants, emulsifiers, foaming agents and mixtures thereof. According to one or more embodiments, the amphiphilic molecule is selected from the group comprising anionic, cationic, nonionic and amphoteric surfactants. According to one or more embodiments, the amphiphilic molecule comprises at least one polar moiety, such as hydrophilic heads, for example selected from the group comprising: carboxylate salts, sulfate salts, sulfonate salts, phosphate ester salts (anionic surfactants); benzalkonium salts, amine salts, quaternary ammonium salts, octenidine salts (cationic surfactants); polypropylene oxides, glucosides, glycerol esters, amine oxides, poloxamers (nonionic surfactants); aminoacids, phospholipids (amphoteric surfactants); and mixture thereof. According to one or more embodiments, the amphiphilic molecule comprises at least one non-polar organic moiety, such as hydrophobic tails, for example selected from the group comprising linear, cyclic or branched, saturated or unsaturated C1-C30 organic moieties. According to one or more embodiments, the C1-C30 organic moieties comprises a C1-C30 alkyl, alkenyl, alkynyl, aryl, alkylaryl, arylalkyl, arylalkenyl or arylalkynyl radical, and optionally comprises one or more heteroatoms such as N, O, S, P, F, Cl, Br and I.

According to one or more embodiments, the amphiphilic molecule comprises a lipid. According to one or more embodiments, the lipid is selected from the group comprising phospholipids, sphingolipids, chelator lipids, antigenic lipids, glycosylated lipids, alkyl phosphate lipids, pH sensitive lipids, adhesive lipids, cross-linking lipids, polyethylene glycol (PEG) phospholipids, PEG ceramides, functionalized PEG lipids and derivative thereof. According to one or more embodiments, the lipid is selected from the group comprising 1,2-bis(10,12-tricosadiynoyl)-sn-glycero-3-phosphocholine, 1,2-bis(10,12-tricosadiynoyl)-sn-glycero-3-phosphoethanolamine, 1-palmitoyl-2-(10,12-tricosadiynoyl)-sn-glycero-3-phosphocholine, 1-palmitoyl-2-(10,12-tricosadiynoyl)-sn-glycero-3-phosphoethanolamine, 1-palmitoyl-2-[16-(acryloyloxy)palmitoyl]-sn-glycero-3-phosphorylcholine.

Figure 1:
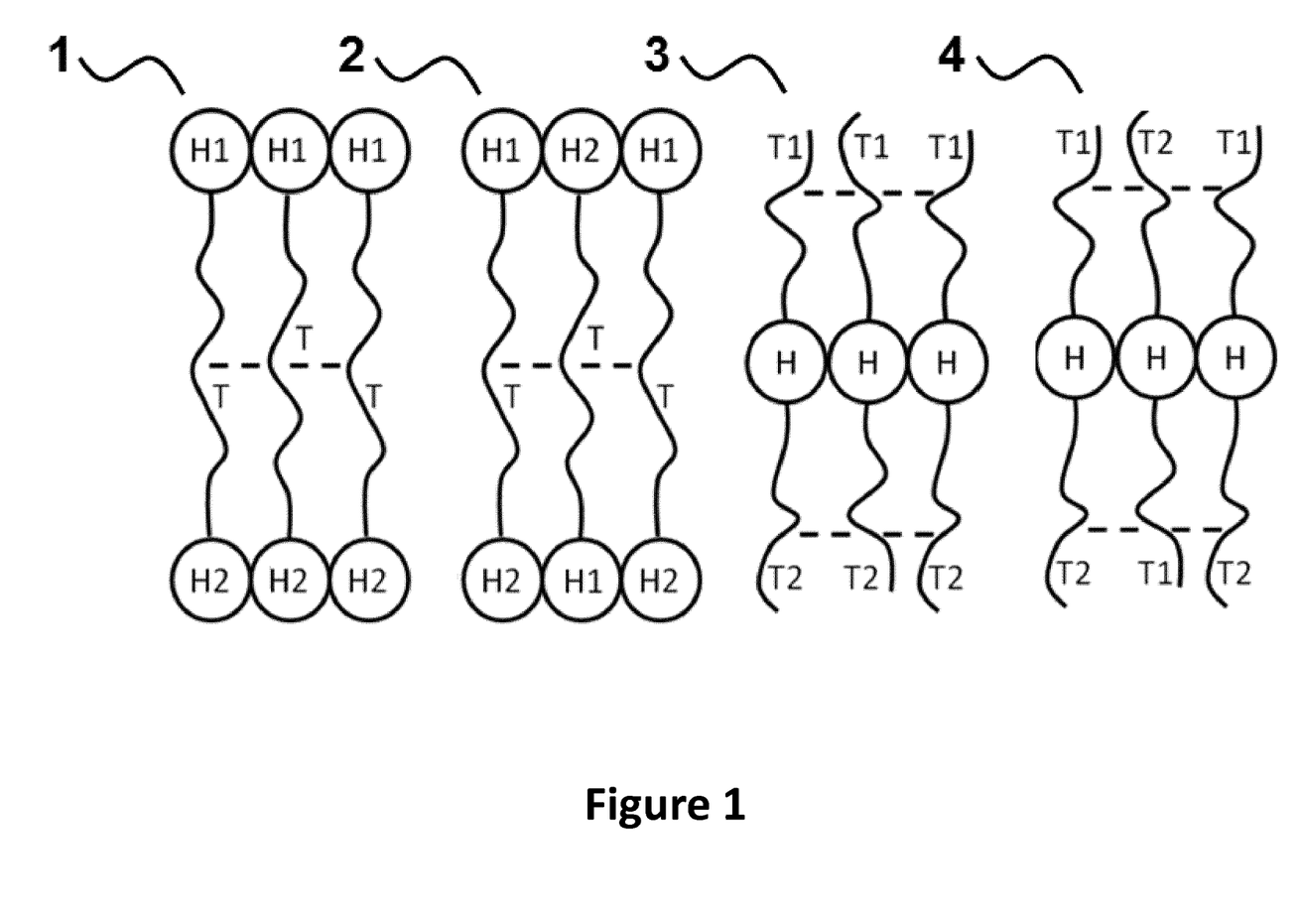
FIG. 1 shows self-assembled bolamphiphilic molecules according to embodiments of the present disclosure.

According to one or more embodiments, the amphiphilic molecules comprise bolamphiphilic molecules. According to one or more embodiments, the bolamphiphilic molecules comprise at least one hydrophobic tail T connecting a first hydrophilic head H1 to a second hydrophilic head H2, the first hydrophilic head H1 and the second hydrophilic head H2 being identical or different. According to one or more embodiments, the bolamphiphilic molecules comprise at least one hydrophilic head H connecting a first hydrophobic tail T1 to a second hydrophobic tail T2, the first hydrophobic tail T1 and the second hydrophobic tail T2 being identical or different. According to one or more embodiments, the first hydrophilic head H1 and the second hydrophilic head H2 are different and the bolamphiphilic molecules are arranged in an non-alternating head-to-head configuration 1 (e.g. [(H1-T-H2)(H1-T-H2)]$_n$) or in a alternating head-to-head configuration 2 (e.g. [(H1-T-H2)(H2-T-H1)]$_n$), as shown in the following FIG. 1. According to one or more embodiments, the first hydrophobic tail T1 and the second hydrophobic tail T2 are different and the bolamphiphilic molecules are arranged in a non-alternating tail-to-tail configuration 3 (e.g. [(T1-H-T2)(T1-H-T2)]$_n$) or in an alternating tail-to-tail configuration 4 (e.g. [(T1-H-T2)(T2-H-T1)]$_n$), as shown in the following FIG. 1.

According to one or more embodiments, the hydrophilic part and/or the hydrophobic part comprise(s) a comonomer moiety and/or a cross-linker bonding the amphiphilic molecules with each other.

According to one or more embodiments, the comonomer moiety or the cross-linker comprises a radical having the following chemical formula:

$$M\text{-}(R)_Y$$

wherein:
M is an element of group 13, 14 or 15 in the periodic table;
R is a functional group, a molecule or a biomolecule; and
Y=1 to 3.

According to one or more embodiments, the comonomer moiety or the cross-linker comprises a radical having the following chemical formula:

$$M\text{-}(R_1)_X(R)_Y$$

wherein:
M is a metal;
R is a functional group, a molecule or a biomolecule;
$R_1$ is a spacer;
X=0, 1, 2 or 3; and
Y=1 to 3.

According to one or more embodiments, M is selected from the group comprising transition metals, metalloids, post-transition metals, phosphorus and nitrogen. According to one or more embodiments, M is selected from the group comprising Si, Ti, Ge, Sn, P and N. According to one or more embodiments, M is an element of group 13, 14 or 15 in the periodic table. According to one or more embodiments, M is selected from the group comprising metalloids, post-transition metals, phosphorus and nitrogen. According to one or more embodiments, M is selected from the group comprising Si, Ge, Sn, P and N. According to one or more embodiments, M is Si or Ge. According to one or more embodiments, M is Si.

According to one or more embodiments, R is a functional group configured for providing to the layer (e.g. at a boundary between a surface of the layer and a condensed phase or a gas phase contacting the layer) at least one predetermined property (e.g. a surface characteristic of the layer). According to one or more embodiments, the predetermined property is selected from the group comprising surface tension, charge density, hydrophobicity, hydrophilicity, wettability, pH, thickness, density, wear resistance, corrosion resistance, chelating, optical, magnetic, redox, insulation and chemical resistance properties.

According to one or more embodiments, the functional group is selected from the group comprising a hydrogen atom, a halide, a linker and an organic compound, such as a linear, cyclic or branched, saturated or unsaturated hydrocarbon. According to one or more embodiments, the functional group is a linker for bonding the layer to a predetermined target, such as a molecule or a biomolecule. According to one or more embodiments, the functional group is a linear, cyclic or branched, saturated or unsaturated C1-C30 organic radical. According to one or more embodiments, the C1-C30 organic radical is a C1-C30 alkyl, alkenyl, alkynyl, aryl, alkylaryl, arylalkyl, arylalkenyl or arylalkynyl radical, and optionally comprises one or more heteroatoms such as N, O, S, P, F, Cl, Br and I.

According to one or more embodiments, $R_1$ is a spacer configured for connecting the comonomer moiety or the cross-linker to an amphiphilic molecule. According to one or more embodiments, the spacer is a linear or branched, saturated or unsaturated C1-C3 organic radical. According to one or more embodiments, the C1-C3 organic radical is a C1-C3 alkyl, alkenyl, alkynyl radical, and optionally comprises one or more heteroatoms such as N, O, S, P, F, Cl, Br and I. According to one or more embodiments, the C1-C3 organic radical is a C1-C3 alkyl and optionally comprises one or more heteroatoms such as N, O, S, P, F, Cl, Br and I.

According to one or more embodiments, X=1, 2 or 3. According to one or more embodiments, 2≤X≤3. According to one or more embodiments, X=2 or 3. According to one or more embodiments, X=3.

According to one or more embodiments, Y=1 or 2. According to one or more embodiments, Y=1.

According to one or more embodiments, the comonomer moiety or the cross-linker forms at least two chemical bonds with the amphiphilic molecules. According to one or more embodiments, the comonomer moiety or the cross-linker is bound to at least two amphiphilic molecules. According to one or more embodiments, the comonomer moiety or the cross-linker is bound to at least two heteroatoms of the self-assembled amphiphilic molecules. According to one or more embodiments, the comonomer moiety or the cross-linker is bound to three heteroatoms of the self-assembled amphiphilic molecules. According to one or more embodiments, M is bound (i.e., by a simple covalent bond) to at least one heteroatom of the at least two amphiphilic molecules. According to one or more embodiments, the comonomer moiety or the cross-linker is bound to at least one first heteroatom of the self-assembled amphiphilic molecules, and the first comonomer moiety or the cross-linker further comprises a second heteroatom bound to at least one second comonomer moiety or cross-linker. According to one or more embodiments, the heteroatom is selected from the group comprising O, S, N and P. According to one or more embodiments, the heteroatom is oxygen. According to one or more embodiments, the comonomer moiety or the cross-linker is bound to the hydrophilic part of the layer.

According to one or more embodiments, the amphiphilic molecule comprises a polymerized functional group selected from the group comprising polymerized diynes and acrylates. According to one or more embodiments, the polymerized function is a diyne. According to one or more embodiments, the hydrophobic tail of the amphiphilic molecule comprises a polymerized functional group, for example selected according to the above-mentioned embodiments.

According to one or more embodiments, the layer has a lifetime of over $10^5$ seconds when being subjected to an electric field of up to about 10 MV/cm. According to one or more embodiments, the layer has a lifetime of over $10^6$ seconds when being subjected to an electric field of up to about 5 MV/cm. According to one or more embodiments, the layer is configured for resisting break-through forces of at least 2 nN. According to one or more embodiments, the layer is configured for resisting break-through forces of at least 3.5 nN.

The present disclosure also relates to the use of a layer according to one or more of the above embodiments in a wide range of applications as described in the following.

According to a second aspect, the present disclosure provides a detecting device comprising a substrate and the layer according to any of the embodiments of the first aspect. For example, the layer may be incorporated into a device comprising a substrate supporting the layer, for use in a detector, a biosensor and the like. According to one or more embodiments, the substrate comprises an inorganic or organic/polymeric material. According to one or more embodiments, the substrate comprises a semi-conductive material. According to one or more embodiments, the substrate comprises a silicon surface or an organic semiconductor surface such as a thin film of 2,7-Dioctyl[1]benzothieno[3,2-b][1]benzothiophene. According to one or more embodiments, the layer may be a monolayer on the substrate. According to one or more embodiments, the layer may be a bilayer on the substrate. According to one or more embodiments, the supported layer has a thickness ranging from about 2 nm to about 8 nm. According to one or more embodiments, the supported layer is a monolayer and/or has a thickness ranging from about 2 nm to about 4 nm. According to one or more embodiments, the supported layer is a bilayer and/or has a thickness ranging from about 4 nm to about 8 nm.

According to one or more embodiments, the device is a field effect transistor comprising the layer according to embodiments of the first aspect as a dielectric layer disposed on a substrate between a source and a drain, thereby forming a gate dielectric as described in US 2014/0264473 A1. According to one or more embodiments, the field effect transistor includes: a semiconducting substrate $2s$ having two areas doped with electric charge carriers forming a source area and a drain area, respectively; a dielectric layer positioned above the semiconducting substrate between the source and the drain and forming the gate dielectric of the field effect transistor; a gate consisting of a reference electrode and of a conductive solution, the solution being in contact with the gate dielectric; the gate dielectric $30o$ comprising a layer according to any of the embodiments of the first aspect in direct contact with the semiconducting layer.

According to a third aspect, one or more of the above-mentioned objects, as well as further advantages, are achieved by a liposome, a micelle, a transport system for a substance (e.g. for delivering an active substance or a drug) and a biomimetic system comprising the layer according any of the embodiments of the first aspect. According to one or more embodiments, the transport system as well as the biomimetic system may comprise a solvent and the layer. According to one or more embodiments, the solvent is aqueous. For example, the layer may be in the form of liposomes and micelles, thereby providing a membrane for encapsulation of the substance, such as an active agent for drug delivery applications. Layers in the form of micellar or lamellar structures may also provide membranes for biomimetic systems aiming at mimicking a cell membrane for biological applications. According to one or more embodiments, the liposomes and/or micelles have an average diameter ranging from about 1 m to about 100 µm. According to one or more embodiments, the liposomes and/or micelles have an average diameter ranging from about 10 µm to about 100 µm.

A process to produce a layer according to any of the embodiments of the first aspect is also provided herein. Specifically, according to a fourth aspect, the present disclosure provides a process for producing a layer, the process comprising: providing amphiphilic molecules; allowing sufficient time for the amphiphilic molecules to self-assemble and form at least one hydrophilic part and at least one hydrophobic part of the layer; and polymerizing the self-assembled amphiphilic molecules with each other on both the hydrophilic part and the hydrophobic part of the layer.

According to one or more embodiments, the polymerizing comprises cross-linking at least one of the hydrophilic part and the hydrophobic part. According to one or more embodiments, the polymerizing comprises polymerizing either one of the hydrophilic part and the hydrophobic part; and cross-linking the other one of the hydrophilic part and the hydrophobic part.

According to one or more embodiments, the polymerizing comprises polymerizing with a comonomer; and/or the cross-linking comprises cross-linking with a cross-linking agent. According to one or more embodiments, the comonomer or the cross-linking agent comprises the following chemical formula:

wherein:
Z is a leaving group;
X=2, 3, or 4; and
M is a metal, such as an element of group 13, 14 or 15 in the periodic table;
R is a functional group, a molecule or a biomolecule;
Y=1 to 3.

According to one or more embodiments, the comonomer or the cross-linking agent comprises the following chemical formula:

wherein:
Z is a leaving group;
X=2, 3, or 4; and
M is a metal;
R is a functional group, a molecule or a biomolecule;
$R_1$ is a spacer;
Y=1 to 3.

According to one or more embodiments, M, R and Y are individually selected as defined in the above embodiments defined with reference of the first aspect.

According to one or more embodiments, Z is selected from the group comprising fluoride, chloride, bromide, iodide, hydroxide, alkoxides, carboxylates, sulfonates, nitrate, phosphate, thiolates, amines, ammonia and dinitrogen. According to one or more embodiments, Z is selected from the group comprising F, Cl, Br, I, OH, OR', OCOR', $OSO_2R'$, $ONO_2$, $OPO(OH)_2$, $SR'_2{}^+$, $NR'_2$, $NR'_3{}^+$, $N_2{}^+$, R' being identical or different and each R' being a hydrogen atom or a linear, cyclic or branched, saturated or unsaturated, substituted or unsubstituted C1-C20 organic radical. According to one or more embodiments, the C1-C20 organic radical is a C1-C20 alkyl, alkenyl, alkynyl, aryl, alkylaryl, arylalkyl, arylalkenyl or arylalkynyl radical, and optionally comprises one or more heteroatoms such as N, O, S, P, F, Cl, Br and I. According to one or more embodiments, Z is selected from the group comprising F, Cl, Br, I and OH. According to one or more embodiments, Z is selected from the group comprising a halogen, a triflate, a tosylate, a mesylate and the like. According to one or more embodiments, Z is a halogen. According to one or more embodiments, Z is Cl.

According to one or more embodiments, the spacer $R_1$ is as defined in the above embodiments defined with reference of the first aspect.

According to one or more embodiments, X=3 or 4. According to one or more embodiments, 2≤X≤3. According to one or more embodiments, X=2 or 3. According to one or more embodiments, X=3.

According to one or more embodiments, the comonomer or the cross-linking agent comprises an organosilicon halide, which may be saturated or unsaturated, cyclic linear or branched, and which may optionally comprise one or more heteroatoms. According to one or more embodiments, the comonomer or the cross-linking agent comprises an organosilicon chloride or bromide. According to one or more embodiments, the comonomer or the cross-linking agent comprises an organosilicon trichloride, such as an alkyl trichlorosilane (e.g. methyltrichlorosilane, octadecyltrichlorosilane and the like).

According to one or more embodiments, the polymerizing or cross-linking comprises bonding the comonomer or the cross-linking agent to at least two nucleophilic functional groups of the self-assembled amphiphilic molecules. According to one or more embodiments, the polymerizing or the cross-linking comprises bonding the comonomer or the cross-linking agent to three nucleophilic functional groups of the self-assembled amphiphilic molecules.

According to one or more embodiments, the polymerizing or the cross-linking comprises bonding M (i.e., by a simple covalent bond) to at least one nucleophilic functional group of at least two amphiphilic molecules. According to one or more embodiments, the nucleophilic functional group is selected from the group comprising hydroxyls, thiols, amines, amides, carboxylic acids and derivative thereof. According to one or more embodiments, the nucleophilic functional group is a hydroxyl. According to one or more embodiments, the polymerizing or the cross-linking comprises bonding the comonomer or the cross-linking agent to the hydrophilic part of the layer.

According to one or more embodiments, the polymerizing and/or the cross-linking is/are performed in a polar organic solvent, an aqueous solvent or mixture thereof. According to one or more embodiments, the polymerizing and/or the cross-linking is/are performed in a solvent selected from the group comprising dioxane, water, tetrahydrofuran and diethyl ether. According to one or more embodiments, the polymerizing and/or cross-linking the hydrophilic part is/are performed in dioxane. According to one or more embodiments, the polymerizing/cross-linking the hydrophobic part is performed in water.

According to one or more embodiments, the polymerizing and/or the cross-linking is/are performed at a temperature ranging from about 20° C. to about 60° C. According to one or more embodiments, the polymerizing and/or the cross-linking is/are performed at a temperature ranging from about 20° C. to about 42° C. According to one or more embodiments, the polymerizing and/or the cross-linking is/are performed for a duration ranging from about 5 minutes to about 24 hours. According to one or more embodiments, the polymerizing and/or the cross-linking is/are performed for a duration ranging from about 10 minutes to about 2 hours. According to one or more embodiments, the polymerizing and/or the cross-linking is/are performed at atmospheric pressure.

According to one or more embodiments, the polymerizing or cross-linking the hydrophobic part is a two-dimensional polymerization or cross-linking. According to one or more embodiments, the polymerizing or cross-linking the hydrophobic part comprises polymerizing or cross-linking a polymerizable functional group, for example a polymerizable functional group of at least one the hydrophobic tails of the hydrophobic parts. According to one or more embodiments, the polymerizable functional group is selected from the group comprising diynes and acrylates. According to one or more embodiments, the polymerizable functional group is a diyne.

According to one or more embodiments, the polymerizing and/or cross-linking the hydrophobic part is/are selected from the group comprising thermal polymerization, photo-polymerization and radical polymerization. According to one or more embodiments, the polymerizing and/or cross-linking the hydrophobic part is/are selected from the group comprising photo-polymerization and radical polymerization. According to one or more embodiments, the polymerizing and/or cross-linking the hydrophobic part is/are a radical polymerization. According to one or more embodiments, the polymerizing and/or cross-linking the hydrophobic part comprise(s) providing a free radical generating compound and allowing sufficient time for the free radical generating compound to initiate the polymerization and/or cross-linking. According to one or more embodiments, the free radical generating compound is selected from the group comprising azo, benzile, metal iodide and metal alkyl compounds. According to one or more embodiments, the free radical generating compound comprises an azo-compound such as ((2,2'-Azobis(2-methylpropionamidine) dihydrochloride.

According to one or more embodiments, the self-assembling is performed through non-covalent interactions (e.g. ionic interactions, r-interactions, hydrogen bonding and dipole-dipole interactions). According to one or more embodiments, the self-assembling comprises self-assembling the amphiphilic molecules to form a monolayer, bi-layer or multi-layer. According to one or more embodiments, the self-assembling comprises self-assembling the amphiphilic molecules to form micellar or lamellar structures. According to one or more embodiments, the self-assembling is performed to form liposomes and/or micelles.

According to one or more embodiments, the self-assembling is performed on a substrate, in an oleaginous solvent such as an oil and/or in a non-oleaginous solvent such as an aqueous solvent or polar solvent. According to one or more embodiments, the self-assembling is performed in a solvent comprising water, a saline solution or a brine.

According to one or more embodiments, the self-assembling is performed at a temperature ranging from about −5° C. to about 60° C. According to one or more embodiments, the self-assembling is performed at a temperature ranging from about −10° C. to about 45° C. According to one or more embodiments, the self-assembling is performed for a duration ranging from about 1 minutes to about 2 hours. According to one or more embodiments, the self-assembling is performed for a duration raging from about 5 minutes to about 1 hour. According to one or more embodiments, the self-assembling is performed at atmospheric pressure.

According to one or more embodiments, the amount of the amphiphilic molecule during the self-assembling ranges from about 0.01 w % to about 1 w % with respect to the weight of the solvent. According to one or more embodiments, the 3o amount of the amphiphilic molecule during the self-assembling ranges from about 0.1% to about 1 w % with respect to the weight of the solvent. According to one or more embodiments, the amount of the copolymer and/or cross-linking agent during the polymerizing and/or cross-linking ranges from about 0.01% to about 10 w % with respect to the weight of the solvent. According to one or more embodiments, the amount of the copolymer and/or cross-linking agent during the polymerizing and/or cross-linking ranges from about 0.1% to about 1 w % with respect to the weight of the solvent.

According to one or more embodiments, the process comprises providing a substrate and forming the layer on the substrate. According to one or more embodiments, the substrate is selected as defined in any of the embodiments defined with reference to the third aspect.

EXAMPLES

Amphiphilic molecules layers and processes according to embodiments of the above aspects are described therein.

Amphiphilic Molecule Preparation

Lipid 1, namely 1,2-bis(10,12-tricosadiynoyl)-sn-glycero-3-phosphocholine, which is commercially available from Avanti®, was modified to present a selected nucleophilic functional group. As illustrated in Scheme 1, the hydrophilic head of lipid 1 was cleaved by enzymatic reaction using a phospholipase, namely phospholipase C to remove the phosphocholine group from the hydrophilic head lipid 1, thereby providing lipid 2, namely 1,2-bis(10,12-tricosadiynoyl)-sn-glycerol, bearing a hydrophilic head with a reactive alcohol moiety. A solution of lipid 2 at 1 mg/mL in chloroform was prepared and stored at −20° C. prior to use.

Scheme 1

Vesicle Preparation

Vesicles were prepared as follows. 50 μL of the solution of lipid 2 was heated to 40° C. to evaporate the chloroform and diluted in 200 μL of deionized water. The resulting aqueous solution was sonicated for 15 minutes and repeatedly extruded through a polycarbonate membrane (100 nm pores) to provide a vesicle solution of well-defined and small unilamellar vesicles.

Amphiphilic Molecules Layer Preparation

Starting from the vesicle solution, three silicon supported lipid monolayers, namely a non-polymerized lipid layer (A; comparative), a single polymerized lipid layer (B; comparative) and a polymerized and cross-linked lipid layer (C), were prepared, the aliphatic chains being oriented towards the silicon substrate and the alcohol group facing the solution.

The non-polymerized lipid layer (A) was prepared as follows. The silicon substrate temperature was set to 25° C. and the native oxide of the silicon was removed by dipping the silicon substrate for 2 minutes in 2% HF. The surface of the substrate was covered by the vesicle solution, which was cooled down to 10° C. and kept at 10° C. for 5 minutes while stirring with a pipette. The non-polymerized lipid layer (A) was found to be unstable in air and to have minimal mechanical stability.

The single polymerized lipid layer (B) was prepared as follows. Starting from the non-polymerized lipid layer (A) covered by the vesicle solution, the temperature of the solution was increased by 1° C./min until 32° C. and rinsed with a 1% (2,2'-Azobis(2-methylpropionamidine) dihydrochloride (AAPH) aqueous solution. The temperature of the resulting mixture was gradually increased and decreased (10 min at 32° C.; 10 min at 35° C.; 10 min to 40° C.; 10 min to 42° C.; 10 min at 38° C.; and 5 min at 35° C.) so as to polymerize the acetylenic groups of the lipid layer, as illustrated in Scheme 2. Lastly, the substrate was rinsed abundantly with water. The single polymerized lipid layer (B) was found to be chemically stable in air, water and methanol and to have some degree of mechanical and electrical stability.

Scheme 2

Scheme 3

To further increase chemical, mechanical and electrical stability, a further level of polymerization was provided by cross-linking the alcohol functional group of the hydrophilic head-group using a trichlorosilane, as illustrated in Scheme 3.

The polymerized and cross-linked lipid layer (C) was prepared as follows. Starting from the single polymerized lipid Layer (B), the surface of the substrate was covered by a solution of a trichlorosilane, namely methyltrichlorosilane (similar result obtained with octadecyltrichlorosilane), in 1,4-dioxane for 15 minutes, as illustrated in Scheme 4. The polymerized and cross-linked lipid layer (C) was found to be chemically stable in air, water, methanol and ethanol as well as in MPR1165 from Shipley™, which is a mixture of organic solvents for removing photoresists. The polymerized and cross-linked lipid layer (C) was also found to have improved mechanical stability, e.g. increase of Young's modulus, and electrical stability, e.g. increase of dielectric breakdown voltage.

Scheme 4

Mechanical Stability of the Amphiphilic Molecules Layer

Figure 2:
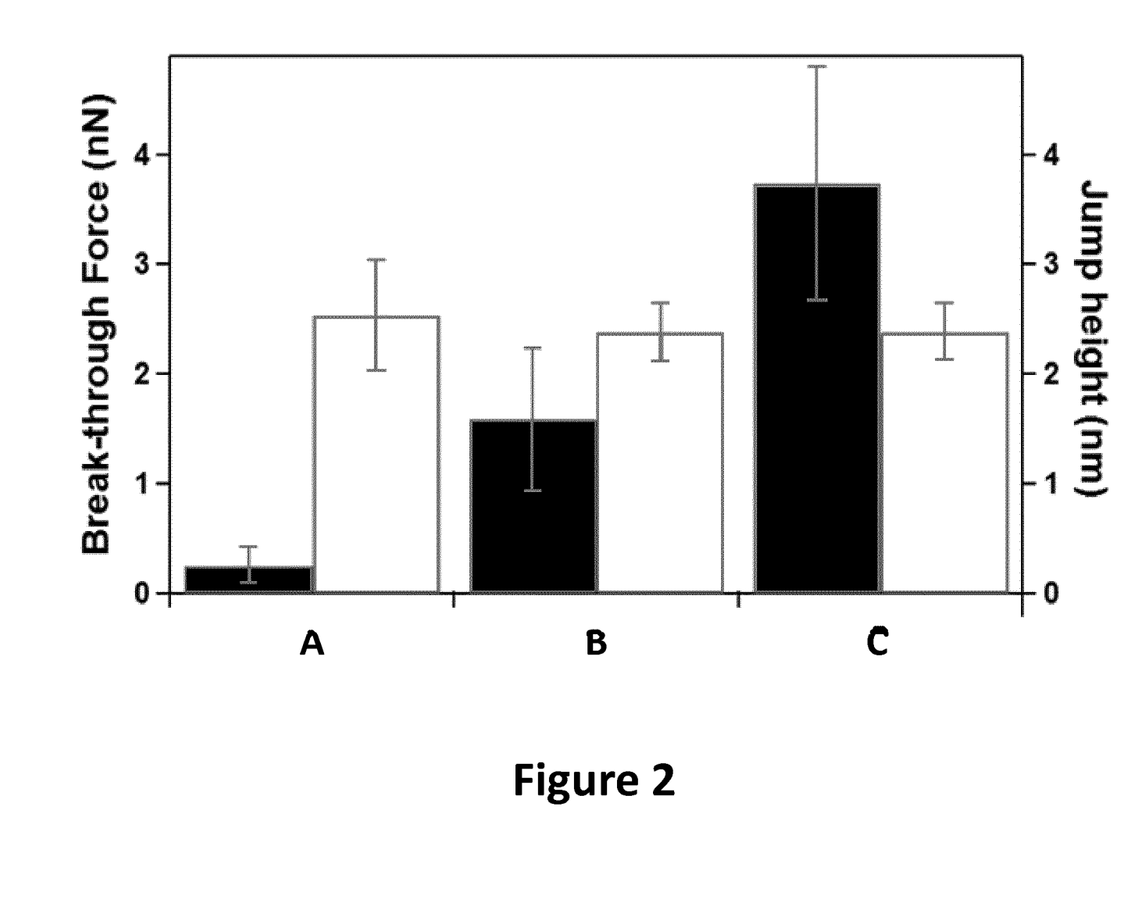
FIG. 2 shows mechanical rupture measurements of a layer according to embodiments of the present disclosure and comparative layers.

Force measurements by Atomic Force Microscopy (AFM) were performed to evaluate the change in mechanical stability of the lipid layers. The experiment consisted in pressing the AFM tip against the lipid layer while increasing the pressure until the lipid layer ruptures. FIG. 2 reports the values obtained for the non-polymerized layer (A), the single polymerized layer (B) and the polymerized and cross-linked layer (C) (black columns are the force required rupturing the monolayer using an AFM tip; white columns are the thickness of the monolayer). As shown in FIG. 2, the polymerized and cross-linked lipid layer (C) was found to have an increase in mechanical stability of about 2.4 times of that of layer B.

Electrical Stability of the Amphiphilic Molecules Layer

Figure 3:
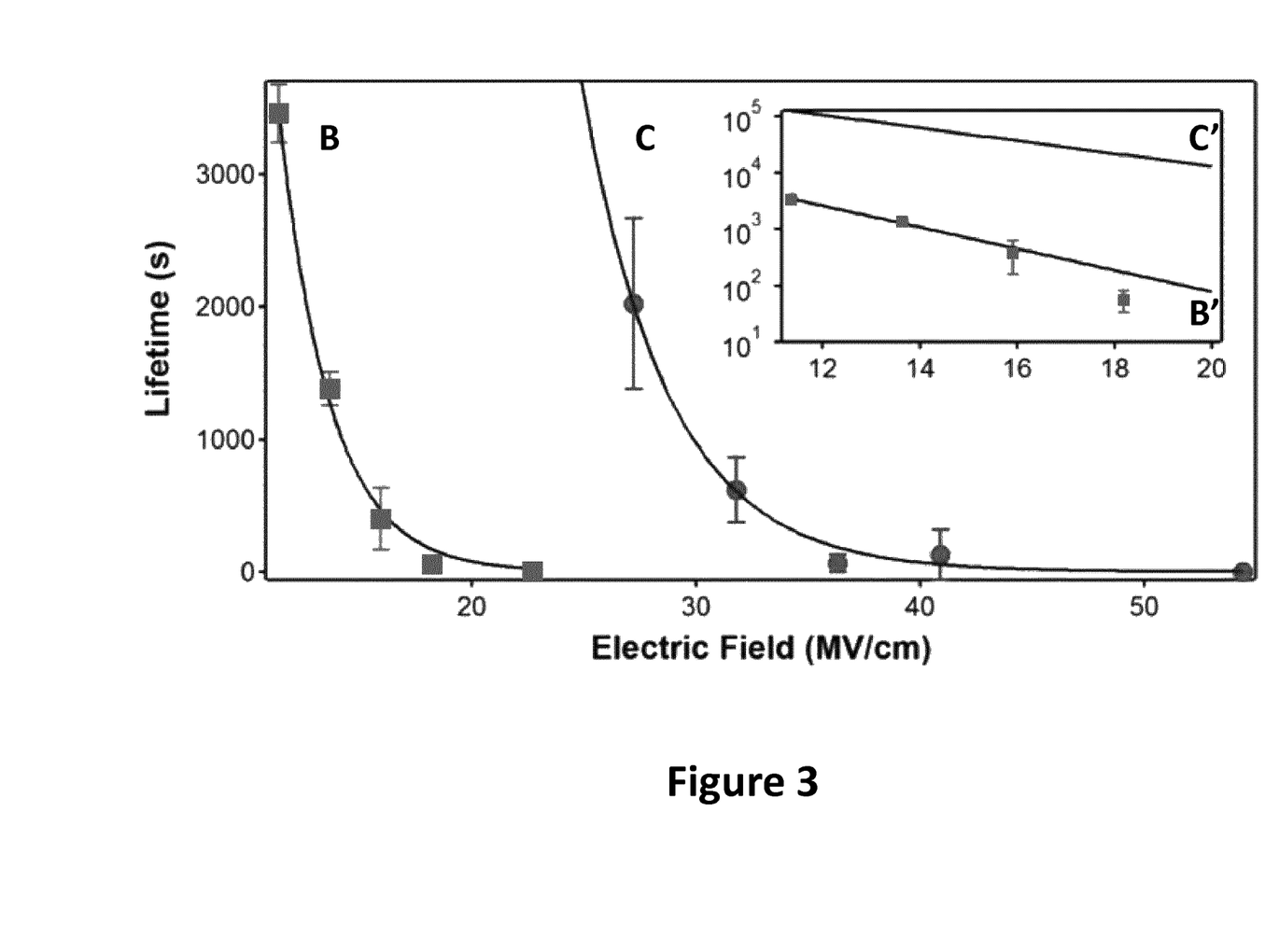
FIG. 3 shows lifetime measurements as a function of applied electric fields on a layer according to embodiments the present disclosure and a comparative layer.

For different electric fields, the lifetime of the single polymerized monolayer (B) and the polymerized and cross-linked monolayer (C) are reported in FIG. 3, which shows the lifetime (i.e., duration before occurrence of dielectric breakdown) of the monolayers at given electric fields. As shown in FIG. 3, the lifetimes of the lipid layers (B and C) decrease exponentially with respect to the applied electric field. However, one can see that, for any given lifetime, the cross-linked layer (C) is able to resist electric fields that are more than twice as high the electric fields applied to the single polymerized layer (B). For example, the cross-linked layer (C) may reach a lifetime of over 1000 seconds when subjected to an electric field of about 30 MV/cm. Conversely, the single polymerized monolayer (B) merely reaches a lifetime of 1000 seconds when an electric field of only 7 MV/cm is applied. Similarly, the cross-linked layer (C) may reach a lifetime of over 3000 seconds when subjected to an electric field of about 25 MV/cm. Conversely, the single polymerized monolayer (B) merely reaches a lifetime of 3000 seconds when an electric field of only 2 MV/cm is applied. The top right inset of FIG. 3 shows an extrapolation of the curves for electric fields ranging from 11 to 20 MV/cm. In this range of electric field, the lifetime of the cross-linked layer (graph C') is at least 50 times longer than for the single polymerized layer (graph B').

Embodiments of the present disclosure provide amphiphilic molecules layers with improved chemical stability. Additionally, because the self-assembled amphiphilic molecules are polymerized with each other on both the hydrophilic part and the hydrophobic part of the layer, improved electrical and mechanical resistance are also achieved. Indeed, the amphiphilic molecules are not only self-assembled through non-covalent interactions, but the amphiphilic molecules are also covalently bound with each other at both their hydrophilic tails and hydrophobic heads. Further, as the amphiphilic molecules may be connected with each other at the hydrophilic part and the hydrophobic part of the layer by simple covalent bonds (i.e., each atom supplying at least one electron to the bond), unforeseeable chemical, mechanical and electrical stabilization may be achieved.

Although the above-mentioned embodiments have been described in detail, it is understood that further embodiments of the disclosure may be envisaged. So for example, embodiments of the layer according to the present disclosure may be prepared from amphiphilic molecules other than a lipid and/or a cross-linking agent other than a trichlorosilane.

The invention claimed is:

1. A layer comprising at least one hydrophilic part and at least one hydrophobic part, the layer comprising self-assembled amphiphilic molecules polymerized with each other on both the hydrophilic part and the hydrophobic part of the layer, wherein the amphiphilic molecules are covalently bound to each other on the hydrophobic part and the amphiphilic molecules are covalently bound to each other through an organosilane cross-linker on the hydrophilic part.

2. The layer according to claim 1, wherein the self-assembled amphiphilic molecules form the at least one hydrophilic part and the at least one hydrophobic part of the layer, wherein said amphiphilic molecules are cross-linked on the hydrophilic part and the hydrophobic part.

3. The layer according to claim 1, wherein the organosilane cross-linker comprises a radical having the following chemical formula:

$$M\text{-}(R_1)_X(R)_Y$$

wherein:

M is Si a metal;

R is an organic compound selected from the group consisting of a linear saturated C1-C30 organic radical, a linear unsaturated C1-C30 organic radical, a cyclic saturated C1-C30 organic radical, a cyclic unsaturated C1-C30 organic radical, a branched saturated C1-C30 organic radical, and a branched unsaturated C1-C30 organic radical;

$R_1$ is O;

X=3; and

Y=1.

4. The layer according to claim 1, wherein the amphiphilic molecules comprise bolamphiphilic molecules.

5. The layer according to claim 1, wherein the organosilane cross-linking agent, prior to crosslinking, comprises the following chemical formula:

$$(Z)_X\text{-}M\text{-}(R)_Y$$

wherein:

Z is a leaving group;

X=3; and

M is Si;

R is an organic compound selected from the group consisting of a linear saturated C1-C30 organic radical, a linear unsaturated C1-C30 organic radical, a cyclic saturated C1-C30 organic radical, a cyclic unsaturated C1-C30 organic radical, a branched saturated C1-C30 organic radical, and a branched unsaturated C1-C30 organic radical;

Y=1.

6. A process for producing the layer of claim 1, the process comprising:

providing the amphiphilic molecules;
allowing sufficient time for the amphiphilic molecules to self-assemble and form the at least one hydrophilic part and the at least one hydrophobic part of the layer; and
polymerizing the self-assembled amphiphilic molecules with each other on both the hydrophilic part and the hydrophobic part of the layer, wherein the polymerizing comprises polymerization of the amphiphilic molecules at the hydrophobic part of the layer and cross-linking at the hydrophilic part of the layer though an organosilane cross-linking agent.

7. A detecting device comprising a substrate and the layer according to claim 1.

8. A liposome comprising the layer according to claim 1.

9. A micelle comprising the layer according to claim 1.

10. A transport system for a substance comprising the liposome according to claim 8.

11. A biomimetic system comprising the liposome according to claim 8.

12. A transport system for a substance comprising the micelle according to claim 9.

13. A biomimetic system comprising the micelle according to claim 9.

* * * * *